(12) United States Patent
Liao (10) Patent No.: US 12,232,814 B2
(45) Date of Patent: Feb. 25, 2025

(54) APPARATUS AND METHOD FOR GENERATING SURFACE CONTOUR OF BONE MODEL, STORAGE MEDIUM, AND ELECTRONIC DEVICE

(71) Applicant: BOE Technology Group Co., Ltd., Beijing (CN)

(72) Inventor: Pingping Liao, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 586 days.

(21) Appl. No.: 17/629,371

(22) PCT Filed: Mar. 5, 2021

(86) PCT No.: PCT/CN2021/079393
§ 371 (c)(1),
(2) Date: Jan. 22, 2022

(87) PCT Pub. No.: WO2021/218383
PCT Pub. Date: Nov. 4, 2021

(65) Prior Publication Data
US 2022/0249169 A1    Aug. 11, 2022

(30) Foreign Application Priority Data

Apr. 30, 2020    (CN) .......................... 202010362867.7

(51) Int. Cl.
*A61B 34/10*    (2016.01)
*A61B 34/20*    (2016.01)

(52) U.S. Cl.
CPC .............. *A61B 34/10* (2016.02); *A61B 34/20* (2016.02); *A61B 2034/105* (2016.02); *A61B 2034/2068* (2016.02)

(58) Field of Classification Search
CPC ... A61B 34/10; A61B 34/20; A61B 2034/105; A61B 2034/2068; G06T 17/00
See application file for complete search history.

(56) References Cited

U.S. PATENT DOCUMENTS

| 6,144,386 A | 11/2000 | Pratt |
| 2007/0249967 A1 | 10/2007 | Buly et al. |

(Continued)

FOREIGN PATENT DOCUMENTS

| CN | 106139423 A | 11/2016 |
| CN | 109223031 A | 1/2019 |

(Continued)

OTHER PUBLICATIONS

International Search Report for PCT/CN2021/079393 Mailed May 17, 2021.

(Continued)

*Primary Examiner* — Jason M Ip
(74) *Attorney, Agent, or Firm* — Ling Wu; Stephen Yang; Ling and Yang Intellectual Property (57) ABSTRACT

An apparatus and method for generating the surface contour of a bone model, a storage medium, and an electronic device. The method comprises: step S101, on the basis of the real-time coordinates of the center of a positioning device acquired by a positioning tracking device, acquiring the real-time coordinate of the tip of a probe moving on the surface of a bone model; and step S102, performing three-dimensional reconstruction on all the real-time coordinates of the tip, so as to obtain a three-dimensional digital model of the surface contour of the bone model.

20 Claims, 3 Drawing Sheets

(56) References Cited

U.S. PATENT DOCUMENTS

| | | | | |
|---|---|---|---|---|
| 2009/0122008 A1* | 5/2009 | Melkis | ............... | G06F 3/03543 |
| | | | | 345/157 |
| 2010/0076306 A1* | 3/2010 | Daigneault | ............ | A61B 34/20 |
| | | | | 600/426 |
| 2015/0104092 A1 | 4/2015 | Flohr et al. | | |
| 2018/0107291 A1 | 4/2018 | Gogarty et al. | | |
| 2021/0077064 A1 | 3/2021 | Zheng | | |
| 2021/0186629 A1 | 6/2021 | Shao et al. | | |

FOREIGN PATENT DOCUMENTS

| | | | |
|---|---|---|---|
| CN | 109844451 | A | 6/2019 |
| CN | 109953828 | A | 7/2019 |
| CN | 109984843 | A | 7/2019 |
| CN | 209673111 | U | 11/2019 |
| CN | 110711030 | A | 1/2020 |
| CN | 110960321 | A | 4/2020 |
| CN | 110969694 | A | 4/2020 |
| CN | 111540043 | A | 8/2020 |
| KR | 1020170046996 | A | 5/2017 |

OTHER PUBLICATIONS

Office Action dated Apr. 8, 2023 for Chinese Patent Application No. 202010362867.7 and English Translation.

* cited by examiner

APPARATUS AND METHOD FOR GENERATING SURFACE CONTOUR OF BONE MODEL, STORAGE MEDIUM, AND ELECTRONIC DEVICE

CROSS-REFERENCE TO RELATED APPLICATIONS

The present application is a U.S. National Phase Entry of International Application No. PCT/CN2021/079393 having an international filing date of Mar. 5, 2021, which claims priority to Chinese patent application No. 202010362867.7, filed on Apr. 30, 2020 and entitled "Apparatus and Method for Generating Surface Profile of Bone Model, Storage Medium, and Electronic Device". The above-identified applications are incorporated herein by reference in their entireties.

TECHNICAL FIELD

Embodiments of the present disclosure relate, but are not limited, to the field of medical education and training, and particularly to an apparatus and method for generating a surface profile of a bone model, a storage medium, and an electronic device.

TECHNICAL FIELD

In many fields such as development and testing of orthopedic surgical robots, digital orthopedic teaching, virtual orthopedic surgery training and the like, a physical bone model needs to be digitally modeled to establish a three-dimensional digital model of the bone model, so as to facilitate surgical simulation and digital teaching. However, human bones are irregularly shaped. Therefore, when a mechanical design method is used, the modeling efficiency of a bone model is quite low, it is very difficult to construct a curved surface, and the accuracy is not so high. When a three-dimensional laser scanner in the field of industry is used to scan the bone model for modeling, an expensive three-dimensional scanning device needs to be bought, so the cost input is excessive for a scenario of teaching or training with a digital bone model.

SUMMARY

The below is a summary about the subject matter described in the present disclosure in detail. The summary is not intended to limit the scope of protection of the claims.

An embodiment of the present disclosure provides an apparatus for generating a surface profile of a bone model, which includes: a probe, a tip of which is configured to be capable of moving on a surface of a bone model; a preset number of positioning apparatuses, arranged at a tail of the probe, the preset number being at least three, and any three of the positioning apparatuses being non-collinear; and a positioning tracking apparatus, configured to acquire real-time center coordinates of the positioning apparatuses.

In an exemplary embodiment, the probe further includes a preset switch, configured to send a preset instruction to an upper computer, the preset instruction at least including a starting instruction and a stopping instruction.

In an exemplary embodiment, the probe is pen-shaped, and a pen point of the pen-shaped probe is capable of leaving a visual mark when moving on the surface of the bone model.

An embodiment of the present disclosure also provides a method for generating a surface profile of a bone model, applied to the above apparatus for generating a surface profile of a bone model, including: acquiring a real-time coordinate of a tip of a probe moving on a surface of a bone model based on real-time center coordinates of positioning apparatuses acquired by a positioning tracking apparatus; and performing three-dimensional reconstruction on all real-time coordinates of the tip to obtain a three-dimensional digital model of a surface profile of the bone model.

In an exemplary embodiment, before the operation of acquiring a real-time coordinate of the tip of a probe moving on a surface of a bone model based on real-time center coordinates of positioning apparatuses acquired by a positioning tracking apparatus, the method further includes: according to a center coordinate of each positioning apparatus and a geometric dimension of the probe, determining a fitting relationship between the center coordinate of the positioning apparatus and a coordinate of the tip.

In an exemplary embodiment, after the operation of determining a fitting relationship between a center coordinate of the positioning apparatus and a coordinate of the tip, the method further includes: calibrating the fitting relationship.

In an exemplary embodiment, the operation of acquiring the real-time coordinate of the tip of a probe moving on a surface of a bone model based on real-time center coordinates of positioning apparatuses acquired by a positioning tracking apparatus includes: determining the real-time coordinate of the tip based on the real-time center coordinates and the fitting relationship.

In an exemplary embodiment, the operation of determining the real-time coordinate of the tip based on the real-time center coordinates and the fitting relationship includes: checking the real-time center coordinates; and determining the real-time coordinate of the tip based on real-time center coordinates passing the checking and the fitting relationship.

In an exemplary embodiment, the method further includes: acquiring the real-time coordinate of the tip of the probe moving on the surface of the bone model based on the real-time center coordinates of the positioning apparatuses acquired by the positioning tracking apparatus when a starting instruction given by the probe is received; and stopping acquiring the real-time coordinate of the tip when a stopping instruction given by the probe is received.

In an exemplary embodiment, the operation of performing three-dimensional reconstruction on all the real-time coordinates of the tip to obtain a three-dimensional digital model of a surface profile of the bone model includes: receiving a reconstruction instruction; and performing three-dimensional reconstruction on all the real-time coordinates of the tip to obtain the three-dimensional digital model of the surface profile of the bone model based on the reconstruction instruction.

An embodiment of the present disclosure also discloses a non-transitory computer-readable storage medium storing a computer program which is executed by a processor to implement the acts of any above-mentioned method.

An embodiment of the present disclosure also discloses an electronic device, which at least includes a memory and a processor, a computer program is stored in the memory, the processor executes the computer program in the memory to implement the acts of any above-mentioned method.

Other aspects will become apparent upon reading and understanding the drawings and the detailed description.

BRIEF DESCRIPTION OF DRAWINGS

The drawings in the following description are only some embodiments recorded in the present disclosure. Those of ordinary skill in the art may further obtain other drawings according to these drawings without paying an inventive effort.

DETAILED DESCRIPTION

The solutions and features of the embodiments of the present disclosure are described herein with reference to the drawings.

It should be understood that various modifications may be made to the embodiments of the present disclosure herein. The contents of the specification are only examples of the embodiments rather than limits. Those skilled in the art can conceive other modifications within the scope and spirit of the present disclosure.

The embodiments of the present disclosure are described hereinafter with reference to the drawings. However, it should be understood that the embodiments of the present disclosure are only examples of the present disclosure and may be implemented in various modes. Well-known and/or repeated functions and structures are not described too much so as to avoid the present disclosure being made ambiguous by unnecessary or redundant details. Structural and functional details described in the embodiments of the present disclosure are not intended to form limits but are used only as the basis of the claims and representative bases to instruct those skilled in the art to use the present disclosure in form of various substantially appropriate detailed structures.

All phrases "in an embodiment", "in another embodiment", "in yet another embodiment" or "in other embodiments" used in the specification may refer to one or more of the same or different embodiments according to the present disclosure.

In many fields such as development and testing of orthopedic surgical robots, digital orthopedic teaching, virtual orthopedic surgery training and the like, a physical bone model needs to be digitally modeled to establish a three-dimensional digital model of the bone model, so as to facilitate surgical simulation and digital teaching. However, human bones are irregularly shaped. Therefore, when a mechanical design method is used, the modeling efficiency of a bone model is quite low, it is very difficult to construct a curved surface, and the accuracy is not so high. When a three-dimensional laser scanner in the field of industry is used to scan the bone model for modeling, an expensive three-dimensional scanning device needs to be bought, so the cost input is excessive for a scenario of teaching or training with a digital bone model.

Accordingly, an embodiment of the present disclosure provides an apparatus for generating a surface profile of a bone model, which includes:

a probe, a tip of which is configured to be capable of moving on a surface of a bone model;

a preset number of positioning apparatuses, wherein the positioning apparatuses are arranged at a tail of the probe, the preset number is at least three, and any three of the positioning apparatuses are non-collinear; and a positioning tracking apparatus, configured to acquire real-time center coordinates of the positioning apparatuses.

Figure 1:
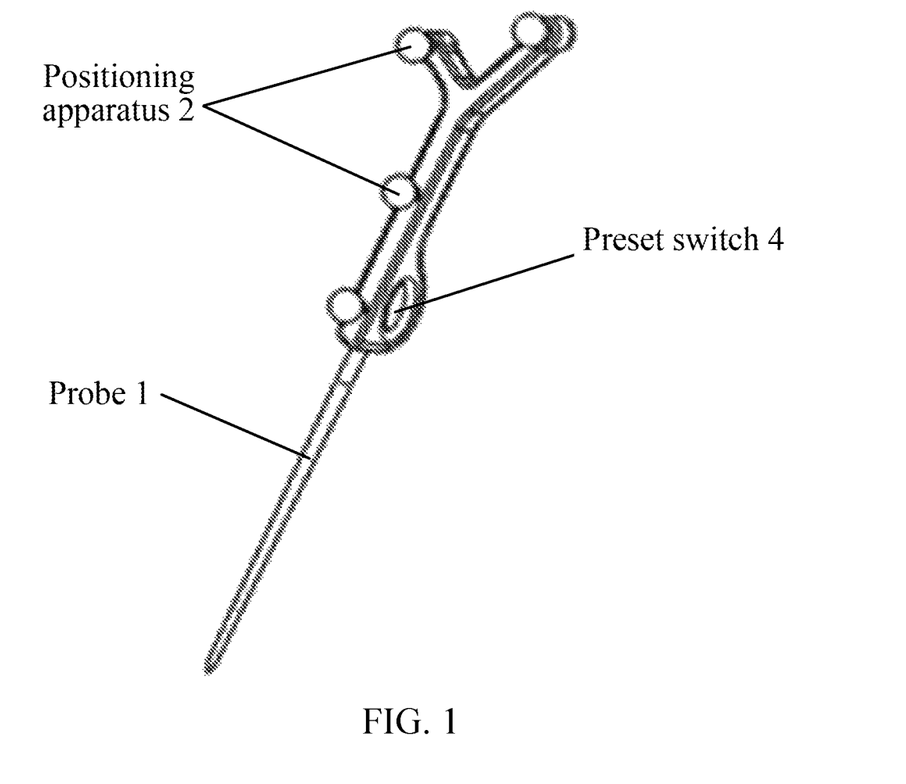
FIG. 1 is a schematic diagram of the structure of a probe and positioning apparatuses according to an embodiment of the present disclosure.

An embodiment of the present disclosure provides an apparatus for generating a surface profile of a bone model, which includes a probe 1, a preset number of positioning apparatuses 2, and a positioning tracking apparatus 3. A tip of the probe 1 is configured to be capable of moving on a surface of a bone model. The probe 1 may be held by a user for operation. The preset number of positioning apparatuses 2 may be spherical positioning members (or the positioning apparatuses 2 may be protruding structures shaped into ellipses, squares, or the like), and may be positioned and recognized by the positioning tracking apparatus 3. The positioning tracking apparatus 3 may be an optical positioning tracking device, and is configured to acquire a real-time center coordinate of each positioning apparatus 2. When the positioning apparatus 2 is a positioning ball, a center coordinate of a ball body is a ball center coordinate of the positioning ball. When the positioning apparatus 2 is a positioning member in another shape, a center coordinate capable of representing the positioning apparatus 2 needs to be determined according to a characteristic of the corresponding shape. The acquisition of the center coordinate of the positioning apparatus in the present embodiment is only an example. In another embodiment, a coordinate of any position of the positioning apparatus, e.g., an edge coordinate of the positioning apparatus, may be acquired as long as a real-time coordinate of a tip may be determined according to a fitting relationship between a coordinate of the positioning apparatus and a coordinate of the tip.

FIG. 1 is a schematic diagram of the structure of the probe 1 and the positioning apparatuses 2. It can be seen from FIG. 1 that the preset number of positioning apparatuses 2 are arranged at a tail (a position away from the tip) of the probe 1. Under a coordinate system of the positioning tracking apparatus 3, the positioning tracking apparatus 3 may directly acquire the center coordinate of the positioning apparatus 2 to represent a present position of the positioning apparatus 2. In order to recognize a pose of the probe 1 accurately, the number of the positioning apparatuses 2 is set to at least three. For positioning a three-dimensional pose of the probe 1, the number of the positioning apparatuses 2 may be set to at most five. In the present embodiment, as shown in FIG. 1, the positioning apparatus 2 is arranged as a positioning ball, and the number of positioning balls at the tail of the probe 1 is set to four. Three of the four positioning balls position a pose of the probe 1, while the other positioning ball implements compensation positioning to improve the pose determination accuracy. In another embodiment, a positioning apparatus for compensation positioning may not be arranged. That is, three positioning balls are arranged to acquire the coordinate of the tip of the probe 1. Alternatively, four positioning balls are arranged to acquire the coordinate of the tip of the probe 1. Any three positioning apparatuses 2 in all the positioning apparatuses 2 are arranged to be non-collinear so as to implement the recognition of the pose of the probe 1 in a space of the optical tracking device. The four positioning balls shown in FIG. 1 are arranged in a shape like "Y", and may be adjusted during practical use as long as any three of the positioning apparatuses are non-collinear. The positioning tracking apparatus 3 is configured to acquire real-time coordinates of the positioning apparatuses 2, and may be a device independent of the probe 1 and the positioning apparatuses 2, e.g., a optical tracking device arranged separately. The schematic diagram of the positioning tracking apparatus 3 is not shown in FIG. 1. The positioning tracking apparatus may be any device with a positioning tracking function, and this is not limited in the present embodiment.

In the present embodiment, the probe head is needle-shaped, for example, as shown in FIG. 1. In another embodiment, the probe head may be spherical. A position at which the spherical head contacts with the bone model is considered as a tip. The shape of the head is not limited in an embodiment of the present disclosure as long as the probe head may move on the surface of the bone model.

In an exemplary embodiment, the probe may be set as pen-shaped, e.g., fountain-pen-shaped. A water suction bag may be arranged in the pen-shaped probe. For another example, the probe may be shaped like a pen container with an inner space capable of accommodating a refill. A pen point of the pen-shaped probe is the tip. The pen-shaped probe may leave a visual mark on the surface of the bone model when moving on the surface of the bone model such that an operator may know that coordinates of which parts of the surface have been collected and coordinates of which parts the surface have not been collected yet. The mark may be erasable, which depends on ink or refill used.

When generating a surface profile of the bone model, the operator may hold the probe 1, and the tip moves on the surface of the bone model. A coordinate of the tip of the probe 1 is acquired as a coordinate of a corresponding point on the surface of the bone model. After the tip moves over all or most of positions on the surface of the bone model, coordinates of points on the surface of the bone model may be determined according to all coordinates of the tip acquired in this process. A digital model of the bone model is obtained by three-dimensional model reconstruction.

Since the probe 1 is held by the operator to move on the surface of the bone model, when the tip is away from the surface of the bone model due to an error, fatigue or the like of the operator, the coordinate of the tip may not be used as a coordinate of a point on the surface of the bone model for model reconstruction. In order to prevent such a case from happening, a preset switch 4 may further be arranged on the probe 1. The operator may actively turn on or turn off the preset switch 4 to send a starting instruction or a stopping instruction to an upper computer. The upper computer may be the positioning tracking apparatus 3. The positioning tracking apparatus 3 may be configured to acquire or start acquiring the center coordinates of the positioning apparatuses 2 on the probe 1 when the starting instruction is received and stop optical tracking when the stopping instruction is received. Alternatively, the upper computer may be a computer capable of communicating with the positioning tracking apparatus 3. The upper computer acquires the center coordinates of the positioning apparatuses 2 from the positioning tracking apparatus 3, starts receiving the center coordinates of the positioning apparatuses 2 sent by the positioning tracking apparatus 3 when the starting instruction is received, and when the stopping instruction is received, refuses to receive the center coordinates of the positioning apparatuses 2 sent by the positioning tracking apparatus 3 or stops determining a corresponding real-time coordinate of the tip based on real-time center coordinates of the positioning apparatuses 2. Therefore, the problem of inaccurate reconstruction of the bone model, which is caused by the fact that the tip is away from the surface of the bone model due to an operational error of the operator and the real-time coordinate of the tip is inconsistent with a coordinate of a point on the surface of the bone model, is solved. The preset switch 4 works together with the upper computer to realize the above-mentioned function. An implementation form of the upper computer may be set as required, and this is not limited in an embodiment of the present disclosure.

According to the present embodiment, the positioning apparatuses that may be acquired by the positioning tracking apparatus are arranged at the tail of the probe to determine the pose and coordinate of the tips of the probe under the coordinate system of the positioning tracking apparatus, so as to determine coordinates of points on the surface of the bone model based on the coordinates of the tip when the tip of the probe passes the surface of the bone model and perform modeling accordingly to obtain a digital bone model rapidly. The apparatus of the present embodiment is easy and convenient to operate, and may implement the accurate digitalization of the bone model without purchasing any additional device.

Figure 2:
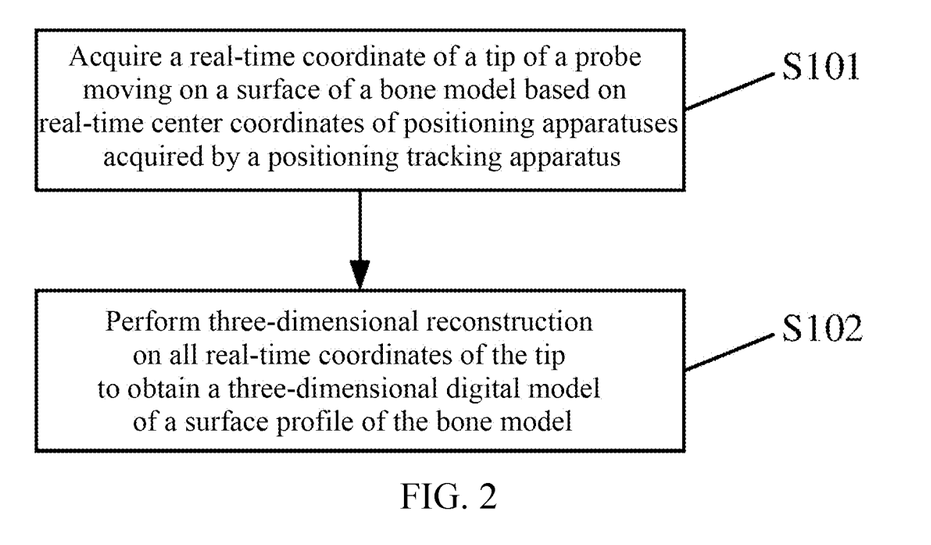
FIG. 2 is a flowchart of a method for generating a surface profile of a bone model according to an embodiment of the present disclosure.

An embodiment of the present disclosure also provides a method for generating a surface profile of a bone model, which is applied to the above-mentioned apparatus for generating a surface profile of a bone model. In the present embodiment, for example, an optical tracking device is used as the positioning tracking apparatus, and a positioning ball is used as the positioning apparatus at the tail of the probe. When the positioning apparatus is a positioning ball, a real-time ball center coordinate of the positioning ball acquired by the optical tracking device is a real-time center coordinate of the positioning apparatus acquired by the positioning tracking apparatus. FIG. 2 is a flowchart of the method for generating a surface profile of a bone model, mainly including acts S101 and S102.

At S101, a real-time coordinate of a tip of the probe moving on a surface of a bone model is acquired based on real-time center coordinates of the positioning apparatuses acquired by the positioning tracking apparatus.

Figure 3:
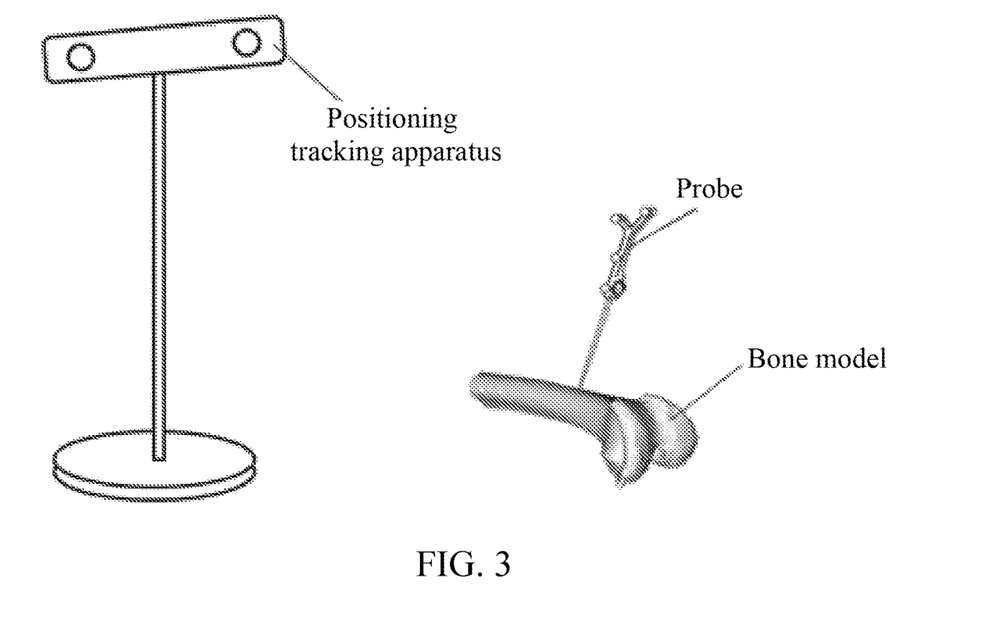
FIG. 3 is a hardware composition diagram of a method for generating a surface profile of a bone model according to an embodiment of the present disclosure.

An optical tracking device is a device which measures and records a motion trail of a target by using an optical measurement and imaging principle, the optical tracking device may obtain a coordinate of an object in a space in a coordinate system of the optical tracking device by shooting or scanning. In the present embodiment, the probe held by an operator moves on a surface of a bone model which needs to be modeled. The optical tracking device acquires real-time ball center coordinates of the positioning balls arranged at the tail of the probe by tracking and scanning. As shown in FIG. 3, a computer terminal communicating with the optical tracking device determines a real-time coordinate of the tip based on fitting relationships between ball center coordinates of multiple positioning balls and a coordinate of the tip of the probe according to the real-time ball center coordinates acquired from the optical tracking device. The tip of the probe keeps in contact with the surface of the bone model, and coordinates of points that the probe passes when moving on the surface of the bone model are the same as real-time coordinates of the tip. Therefore, by acquiring the real-time coordinates of the tip, the coordinates of the corresponding points on the surface of the bone model may be determined. The more completely the probe traverses the surface of the bone model and correspondingly the more the passed points on the surface of the bone model are, the more accurately a reconstructed digital bone model finally can be improved.

Figure 4:
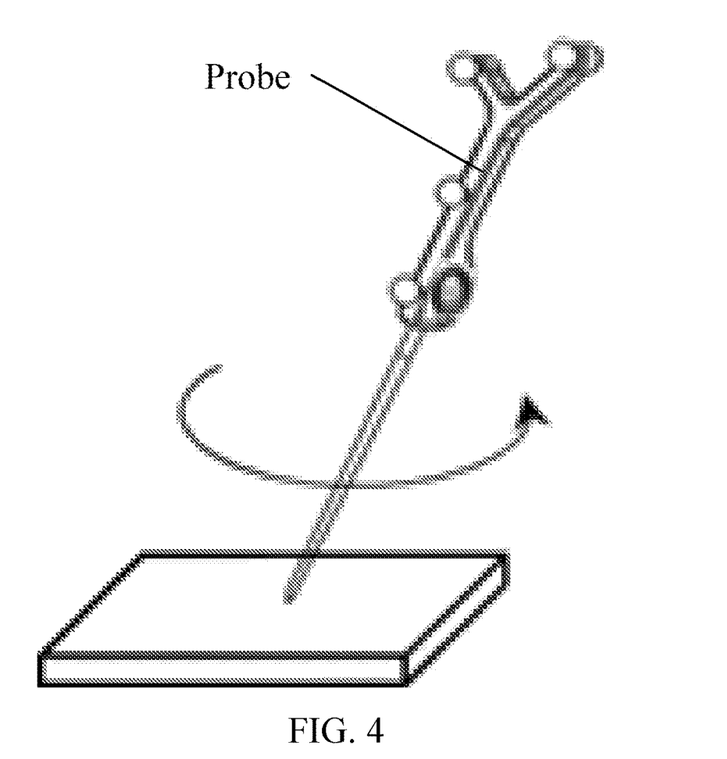
FIG. 4 is a schematic operation diagram of a rotation method according to an embodiment of the present disclosure.

The fitting relationships between the ball center coordinates of the multiple positioning balls and the coordinate of the tip of the probe (i.e., fitting relationships between center coordinates of the positioning apparatuses and a coordinate of the tip of the probe) may be determined according to the ball center coordinate of each positioning ball and a geometric dimension of the probe. Since a distance between each positioning ball and the tip of the probe and a position thereof are fixed, the fitting relationship between the positioning ball and the coordinate of the tip may be determined based on the position of the positioning ball and the distance from the tip. There is a fitting relationship between the ball center coordinate of each positioning ball and the coordinate of the tip. The fitting relationships between the ball center coordinates of different positioning balls and the coordinate of the tip are different. However, the same coordinate of the tip is determined based on the ball center coordinates of different positioning balls and the corresponding fitting relationships. Therefore, the fitting relationship is calibrated by a rotation method in the present embodiment, to improve the fitting accuracy. As shown in FIG. 4, the tip of the probe is fixed to a point within the space of the optical tracking device. Then, the probe is held to rotate for many circles around the tip (for example, rotating in the arrow direction in FIG. 4). The optical tracking device records motion trails of ball center coordinates of all the positioning balls in a rotation process. A motion trail of a ball center of one positioning ball is selected arbitrarily from all the positioning balls. It can be seen from a geometric relationship that the motion trail of the ball center coordinate of the positioning ball should be on a ball with the tip as the ball center, and a radius of the ball is a distance between the tip and the ball center of the positioning ball. By fitting the ball, a ball center coordinate of the fitted ball is a coordinate of the tip of the probe, and the fitting relationship may be calibrated accordingly. The fitting relationship may be calibrated by other methods during practical applications, and this is not limited in an embodiment of the present disclosure.

When the tip of the probe moves on the surface of the bone model, the optical tracking device keeps acquiring real-time ball center coordinates of the positioning balls on the probe. After acquiring the real-time ball center coordinates of the positioning balls, another computer terminal communicating with the optical tracking device may check the real-time ball center coordinates of the positioning balls to reject abnormal data caused by communication abnormality and the like, e.g., abnormal real-time ball center coordinate data brought by temporary interruptions and failures of network communications between the optical tracking device and the computer terminal. Whether there is an abnormality may be judged by a check bit of real-time ball center coordinate data, or by other parameters such as the integrity and data packet length of the real-time ball center coordinate data. For a real-time ball center coordinate passing the checking, a real-time coordinate of the tip may be determined based on the fitting relationship. For a real-time ball center coordinate not passing the checking, the data is directly deleted.

At S102, three-dimensional reconstruction is performed on all real-time coordinates of the tip to obtain a three-dimensional digital model of a surface profile of the bone model.

The tip contacts with the surface of the bone model, and a real-time coordinate of the tip is equivalent to a coordinate of a point where the tip contacts with the surface of the bone model at present. Therefore, all real-time coordinates of the tip determined when the tip moves on the surface of the bone model are coordinates of points overlapped with the tip on the surface of the bone model at corresponding moments. After the probe held by an operator moves over all or most of positions on the surface of the bone model, three-dimensional reconstruction may be performed based on all the real-time coordinates of the tip to finally generate the three-dimensional digital model of the surface profile of the bone model. During the development and testing of orthopedic surgical robots, digital orthopedic teaching and virtual orthopedic surgery training, the three-dimensional digital model may be called for corresponding surgical robot testing, digital teaching, virtual surgery training, or the like.

In the present embodiment, the probe is improved such that an optical positioning device (e.g., the positioning tracking apparatus in the present embodiment) may acquire the probe and determine the real-time coordinate of the tip. When the tip of the probe passes the surface of the bone model, the tip is overlapped with a point on the surface of the bone model, and a real-time coordinate of the tip is equivalent to a coordinate of the point on the surface of the bone model. Real-time coordinates of the tip may be continuously acquired to obtain coordinates of multiple points on the surface of the bone model. Modeling may be performed accordingly to obtain a digital bone model rapidly. The method of the present embodiment is easy and convenient to operate, and the bone model may be digitalized accurately without purchasing any additional device.

Since the probe is held by the operator to move on the surface of the bone model, when the tip is away from the surface of the bone model due to an error, fatigue or the like of the operator, the coordinate of the tip may not be used as a coordinate of a point on the surface of the bone model for model reconstruction. In order to prevent such a case from happening, a preset switch may be arranged on the probe. The operator may actively turn on or turn off the preset switch to send a starting instruction or a stopping instruction to an upper computer. The upper computer may be an optical tracking device such as a positioning tracking apparatus. The positioning tracking apparatus may be configured to acquire or start acquiring the center coordinates of the positioning apparatuses on the probe when the starting instruction is received and stop optical tracking when the stopping instruction is received. Alternatively, the upper computer may be a computer terminal capable of communicating with the positioning tracking apparatus. The upper computer acquires real-time center coordinates of the positioning apparatuses from the positioning tracking apparatus. The upper computer, when receiving the starting instruction, communicates with the positioning tracking apparatus, receives the real-time center coordinates of the positioning apparatuses sent by the positioning tracking apparatus, and correspondingly determines a real-time coordinate of the tip. The upper computer, when receiving the stopping instruction, refuses to receive the real-time center coordinates of the positioning apparatuses sent by the positioning tracking apparatus, or stops determining the corresponding real-time coordinate of the tip based on the real-time center coordinates of the positioning apparatuses. Therefore, the problem of inaccurate reconstruction of the bone model, which is caused by the fact that the tip is away from the surface of the bone model due to an operational error of the operator and the real-time coordinate of the tip is inconsistent with a coordinate of a point on the surface of the bone model, is solved.

For the reconstruction of a complete bone model, the operator may implement multiple starts and interruptions during an operation process to adjust the position of the probe or have a rest. Three-dimensional reconstruction may be performed more accurately after the probe moves over most of positions on a surface of the bone model. Therefore, a reconstruction instruction may be sent to represent that the bone model is completely traversed. The computer terminal, after receiving the reconstruction instruction, performs three-dimensional reconstruction based on the reconstruction instruction and all real-time coordinates of the tip acquired before to obtain a three-dimensional digital model of a surface profile of the bone model. The reconstruction instruction may be sent through the probe. For example, the operator may double-click a preset switch arranged on the probe or long press the preset switch to generate the reconstruction instruction representing that traversing is completed, alternatively, the operator directly operates the computer terminal to generate the reconstruction instruction by clicking a preset button on the computer terminal.

An embodiment of the present disclosure also provides a non-transitory storage medium. The storage medium is a computer-readable medium, and stores a computer program. The computer program, when executed by a processor, implements a method for generating a surface profile of a bone model provided in an embodiment of the present disclosure based on the apparatus for generating a surface profile of a bone model in the above-mentioned embodiment of the present disclosure, including the following acts S11 and S12.

In S11, a real-time coordinate of a tip of the probe moving on a surface of a bone model is acquired based on real-time center coordinates of the positioning apparatuses acquired by the positioning tracking apparatus.

In S12, three-dimensional reconstruction is performed on all real-time coordinates of the tip to obtain a three-dimensional digital model of a surface profile of the bone model.

In an exemplary embodiment, before the computer program is executed by the processor to implement the act of acquiring a real-time coordinate of the tip of a probe moving on a surface of a bone model based on real-time center coordinates of positioning apparatuses acquired by a positioning tracking apparatus, the computer program may further be executed by the processor to implement the following act: according to a center coordinate of each positioning apparatus and a geometric dimension of the probe, determining a fitting relationship between the center coordinate of the positioning apparatus and a coordinate of the tip.

In an exemplary embodiment, when the computer program is executed by the processor to implement the act of acquiring a real-time coordinate of the tip of a probe moving on a surface of a bone model based on real-time center coordinates of positioning apparatuses acquired by a positioning tracking apparatus, the computer program may further be executed by the processor to implement the following act: determining the real-time coordinate of the tip based on the real-time center coordinates and the fitting relationship.

In an exemplary embodiment, when the computer program is executed by the processor to implement the act of determining the real-time coordinate of the tip based on the real-time center coordinates and the fitting relationship, the computer program is may further be executed by the processor to implement the following acts: checking the real-time center coordinate; and determining the real-time coordinate of the tip based on real-time center coordinates passing the checking and the fitting relationship.

In an exemplary embodiment, the computer program may further be executed by the processor to implement the following acts: acquiring the real-time coordinate of the tip of the probe moving on the surface of the bone model based on the real-time center coordinates of the positioning apparatuses acquired by the positioning tracking apparatus when a starting instruction given by the probe is received; and stopping acquiring the real-time coordinate of the tip when a stopping instruction given by the probe is received.

In an exemplary embodiment, when the computer program is executed by the processor to implement the act of performing three-dimensional reconstruction on all real-time coordinate of the tips to obtain a three-dimensional digital model of a surface profile of the bone model, the computer program may be executed by the processor to implement the following acts: receiving a reconstruction instruction; and performing three-dimensional reconstruction on all the real-time coordinates of the tip to obtain the three-dimensional digital model of the surface profile of the bone model based on the reconstruction instruction.

In the present embodiment, the probe is improved such that an optical positioning device may acquire the probe and determine the real-time coordinate of the tip of the probe. When the tip of the probe passes the surface of the bone model, the tip is overlapped with a point on the surface of the bone model, and a real-time coordinate of the tip is equivalent to a coordinate of the point on the surface of the bone model. Real-time coordinates of the tip may be continuously acquired to obtain coordinates of multiple points on the surface of the bone model. Modeling may be performed accordingly to obtain a digital bone model rapidly, operations are simple and easy, and the bone model may be digitalized accurately without purchasing any additional device.

Figure 5:
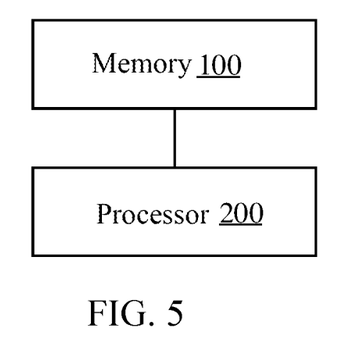
FIG. 5 is a schematic diagram of the structure of an electronic device according to an embodiment of the present disclosure.

An embodiment of the present disclosure also provides an electronic device. FIG. 5 is a schematic diagram of the structure of the electronic device, at least including a memory 100 and a processor 200. A computer program is stored in the memory 100. The processor 200 executes the computer program in the memory 100 to implement the method provided in any embodiment of the present disclosure. For example, the computer program of the electronic device includes the following acts S21 and S22.

In S21, a real-time coordinate of a tip of a probe moving on a surface of a bone model is acquired based on real-time center coordinates of positioning apparatuses acquired by a positioning tracking apparatus.

In S22, three-dimensional reconstruction is performed on all real-time coordinates of the tip to obtain a three-dimensional digital model of a surface profile of the bone model.

In an exemplary embodiment, before the processor executes the computer program in the memory to implement the operation of acquiring a real-time coordinate of the tip of a probe moving on a surface of a bone model based on real-time center coordinates of positioning apparatuses acquired by a positioning tracking apparatus, the processor may further execute the computer program to implement the following operation: according to a center coordinate of each positioning apparatus and a geometric dimension of the probe, determining a fitting relationship between the center coordinate of the positioning apparatus and a coordinate of the tip.

In an exemplary embodiment, when the processor executes the computer program in the memory to implement the operation of acquiring a real-time coordinate of the tip of a probe moving on a surface of a bone model based on real-time center coordinates of positioning apparatuses acquired by a positioning tracking apparatus, the processor may further execute the computer program to implement the following operation: determining the real-time coordinate of the tip based on the real-time center coordinates and the fitting relationship.

In an exemplary embodiment, when the processor executes the computer program in the memory to implement the operation of determining the real-time coordinate of the tip based on the real-time center coordinates and the fitting relationship, the processor may further execute the computer program to implement the following operations: checking the real-time center coordinate; and determining the real-time coordinate of the tip based on real-time center coordinates passing the checking and the fitting relationship.

In an exemplary embodiment, the processor may further execute the computer program in the memory to implement the following operations: acquiring the real-time coordinate of the tip of the probe moving on the surface of the bone model based on the real-time center coordinates of the positioning apparatuses acquired by the positioning tracking apparatus when a starting instruction given by the probe is received; and stopping acquiring the real-time coordinate of the tip when a stopping instruction given by the probe is received.

In an exemplary embodiment, when the processor executes the computer program in the memory to implement the operation of performing three-dimensional reconstruction on all real-time coordinates of the tip to obtain a three-dimensional digital model of a surface profile of the bone model, the processor may further execute the computer program to implement the following operations: receiving a reconstruction instruction; and performing three-dimensional reconstruction on all the real-time coordinates of the tip to obtain the three-dimensional digital model of the surface profile of the bone model based on the reconstruction instruction.

In the present embodiment, the probe is improved such that the positioning tracking apparatus may acquire the probe in real time and determine the real-time coordinate of the tip of the probe. When the tip of the probe passes the surface of the bone model, the tip is overlapped with a point on the surface of the bone model, and a real-time coordinate of the tip is equivalent to a coordinate of the point on the surface of the bone model. Real-time coordinates of the tip may be continuously acquired to obtain coordinates of multiple points on the surface of the bone model. Modeling may be performed accordingly to obtain a digital bone model rapidly, operations are simple and easy, and the bone model may be digitalized accurately without purchasing any additional device.

In some implementation modes, the client and the server may communicate with any currently known network protocol such as Hyper Text Transfer Protocol (HTTP) or any network protocol to be developed in the future, and may be interconnected with a digital data communication network of any form or medium (e.g., a communication network). Examples of the communication network include a Local Area Network (LAN), a Wide Area Network (WAN), an international network (e.g., the Internet), a peer-to-peer network (e.g., an ad hot peer-to-peer network), and any currently known network or network to be developed in the future.

The storage medium may be included in the electronic device, or exist independently but is not assembled in the electronic device.

The computer program codes used for executing operations in an embodiment of the present disclosure may be edited by one or more program design languages or combinations thereof. The program design language includes, but is not limited to, an object-oriented program design language such as Java, Smalltalk and C++, and also includes a conventional procedural program design language such as "C" language or a similar program design language. The computer codes may be completely executed in a user computer, partially executed in the user computer, executed as an independent software package, executed partially in the user computer and partially in a remote computer, or executed completely in the remote computer or a server. In a case involving a remote computer, the remote computer may be connected to the user computer through any type of network including a LAN or a WAN, or, may be connected to an external computer (e.g., connected by an Internet service provider through the Internet).

The storage medium of the present disclosure may be a computer-readable signal medium or a computer-readable storage medium or any combination of the two. The computer-readable storage medium may be, but is not limited to, for example, an electrical, magnetic, optical, electromagnetic, infrared, or semiconductor system, apparatus or device, or any combination thereof. Examples of the computer-readable storage medium may include, but is not limited to, an electrical connector with one or more wires, a portable computer disk, a hard disk, a Random Access Memory (RAM), a Read-Only Memory (ROM), an Erasable Programmable ROM (EPROM) (or a flash memory), an optical fiber, a portable Compact Disc Read-Only Memory (CD-ROM), an optical storage device, a magnetic storage device, or any proper combination thereof. In an embodiment of the present disclosure, the computer-readable storage medium may be any physical medium including or storing a program which may be used by or in combination with an instruction execution system, apparatus or device. In an embodiment of the present disclosure, the computer-readable signal medium may include a data signal in a baseband or propagated as a part of a carrier, with computer-readable program codes carried therein. Multiple forms may be used for the propagated data signal, including, but not limited to, an electromagnetic signal, an optical signal, or any proper combination. Alternatively, the computer-readable signal medium may be any storage medium except the computer-readable storage medium, and may be used to send, propagate or transmit a program used by or in combination with an instruction execution system, apparatus or device. The program codes in the storage medium may be transmitted by any proper medium, including, but not limited to, an electric wire, an optical cable, Radio Frequency (RF), etc., or any proper combination thereof.

The flowcharts and block diagrams in the drawings illustrate probably-implemented system architectures, functions and operations of the system, method and computer program product according to embodiments of the present disclosure. On this aspect, each block in the flowcharts or the block diagrams may represent a module, a program segment or part of codes, and the module, the program segment, or the part of codes includes one or more executable instructions used for realizing a specified logical function. In some alternative implementations, the functions marked in the blocks may be realized in a sequence different from that marked in the drawings. For example, two continuous blocks may actually be executed substantially concurrently, or may be executed in a reverse sequence sometimes, which is determined by the involved functions. Each block in the block diagrams and/or the flowcharts and a combination of the blocks in the block diagrams and/or the flowcharts may be implemented by a dedicated hardware-based system used for executing a specified function or operation, or may be implemented by a combination of dedicated hardware and computer instructions.

The units involved in the embodiments of the present disclosure may be implemented by software or hardware. A name of a unit does not form limit on the unit in some cases.

The above-described functions herein may be at least partially executed by one or more hardware logic components. Exemplarily but unrestrictively, examples of the hardware logic component may include a Field-Programmable Gate Array (FPGA), an Application Specific Integrated Circuit (ASIC), an Application Specific Standard Product (ASSP), a System On Chip (SOC), a Complex Programmable Logic Device (CPLD), etc.

In the context of the embodiments of the present disclosure, the machine-readable medium may be a physical medium, and may include or store a program used by or in combination with an instruction execution system, apparatus or device. The machine-readable medium may be a machine-readable signal medium or a machine-readable storage medium. The machine-readable medium may include, but is not limited to, an electronic, magnetic, optical, electromagnetic, infrared or semiconductor system, apparatus or device, or any proper combination thereof. Examples of the machine-readable storage medium may include an electrical connection based on one or more wires, a portable computer disk, a hard disk, a Random Access Memory (RAM), a Read-Only Memory (ROM), an Erasable Programmable ROM (EPROM) (or a flash memory), an optical fiber, a portable Compact Disc Read-Only Memory (CD-ROM), an optical storage device, a magnetic storage device, or any proper combination thereof.

The above is only description about the embodiments of the present disclosure and adopted technical principles. Those skilled in the art should know that the scope of disclosure involved in the embodiments of the present disclosure is not limited to the technical solutions formed by specifically combining the above-mentioned technical features and shall cover other technical solutions formed by freely combining the above-mentioned technical features or equivalent features thereof without departing from the concept of the present disclosure, for example, technical solutions formed by interchanging the above-mentioned features and (but not limited to) the technical features with similar functions disclosed in the embodiments of the present disclosure.

Although multiple operations are described in a specific order, it should not be explained that these operations are required to be executed in the shown specific order or in sequence. In a certain environment, multi-task and concurrent-processing may be favorable. Multiple implementation details are included in the above discussion, but they should not be explained as limits to the scope of the embodiments of the present disclosure. Some features described in the context of an independent embodiment may be combined for implementation in a single embodiment. Multiple features described in the context of a single embodiment may be implemented in multiple embodiments independently or in form of any proper sub-combination.

Although the subject matter has been described with a language specific to the structural features and/or logic operations in the method, it should be understood that the subject matter defined in the appended claims is not limited to the above-described specific features or operations. The above-described specific features and operations are only example forms for implementing the claims.

Multiple embodiments of the present disclosure are described above but not intended to limit the present disclosure. Those skilled in the art may make various transformations and modifications based on the concept of the present disclosure. These transformations and modifications shall fall in the scope of protection disclosed in the document.

The invention claimed is:

1. An apparatus for generating a surface profile of a bone model, comprising:
    a probe, a tip of which is configured to be capable of moving on a surface of a bone model;
    at least three positioning apparatuses, wherein the positioning apparatuses are arranged at a tail of the probe, and any three of the positioning apparatuses are non-collinear, and the positioning apparatuses are positioning balls;
    a positioning tracking apparatus, configured to acquire real-time center coordinates of the at least three positioning apparatuses; and
    at least one processor, configured to acquire a real-time coordinate of the tip of the probe moving on the surface of the bone model based on the real-time center coordinates of the at least three positioning apparatuses acquired by the positioning tracking apparatus; and perform three-dimensional reconstruction on all real-time coordinates of the tip to obtain a three-dimensional digital model of the surface profile of the bone model;
    wherein the at least one processor is further configured to: according to a center coordinate of each positioning apparatus and a geometric dimension of the probe, determine a fitting relationship between the center coordinates of the at least three positioning apparatuses and the coordinate of the tip; calibrate the fitting relationship; and determine the real-time coordinate of the tip based on the real-time center coordinates of the at least three positioning apparatuses and the calibrated fitting relationship;
    wherein the at least one processor is configured to calibrate the fitting relationship through a following process: fixing the tip of the probe to a point within a space of the positioning tracking apparatus; holding the probe to rotate for at least two circles around the tip; recording, by the positioning tracking apparatus, motion trails of ball center coordinates of all the positioning balls in a rotation process; selecting a motion trail of a ball center of one positioning ball arbitrarily from all the positioning balls, the motion trail of a ball center coordinate of the selected positioning ball being on a ball with the tip as the ball center, and a radius of the ball being a distance between the tip and the ball center of the selected positioning ball; fitting the ball, a ball center coordinate of the fitted ball being the coordinate of the tip of the probe, and calibrating the fitting relationship accordingly.

2. The apparatus for generating a surface profile of a bone model according to claim 1, wherein the probe further comprises:
    a preset switch, configured to send a preset instruction to an upper computer, the preset instruction at least comprising a starting instruction and a stopping instruction.

3. The apparatus for generating a surface profile of a bone model according to claim 1, wherein the probe is pen-shaped, and a pen point of the pen-shaped probe is capable of leaving a visual mark when moving on the surface of the bone model.

4. A method for generating a surface profile of a bone model, applied to the apparatus for generating a surface profile of a bone model according to claim 1, comprising:
  acquiring a real-time coordinate of a tip of the probe moving on a surface of a bone model based on real-time center coordinates of the positioning apparatuses acquired by the positioning tracking apparatus; and
  performing three-dimensional reconstruction on all real-time coordinates of the tip to obtain a three-dimensional digital model of a surface profile of the bone model.

5. The method according to claim 4, wherein before acquiring the real-time coordinate of the tip of the probe moving on the surface of the bone model based on the real-time center coordinates of the positioning apparatuses acquired by the positioning tracking apparatus, the method further comprises:
  according to a center coordinate of each positioning apparatus and a geometric dimension of the probe, determining a fitting relationship between the center coordinate of the positioning apparatus and a coordinate of the tip.

6. The method according to claim 5, wherein after determining the fitting relationship between the center coordinate of the positioning apparatus and the coordinate of the tip, the method further comprises:
  calibrating the fitting relationship.

7. The method according to claim 5, wherein acquiring the real-time coordinate of the tip of the probe moving on the surface of the bone model based on the real-time center coordinates of the positioning apparatuses acquired by the positioning tracking apparatus comprises:
  determining the real-time coordinate of the tip based on the real-time center coordinates and the fitting relationship.

8. The method according to claim 7, wherein determining the real-time coordinate of the tip based on the real-time center coordinates and the fitting relationship comprises:
  checking the real-time center coordinates; and
  determining the real-time coordinate of the tip based on real-time center coordinates passing the checking and the fitting relationship.

9. The method according to claim 4, further comprising:
  acquiring the real-time coordinate of the tip of the probe moving on the surface of the bone model based on the real-time center coordinates of the positioning apparatuses acquired by the positioning tracking apparatus when a starting instruction given by the probe is received; and
  stopping acquiring the real-time coordinate of the tip when a stopping instruction given by the probe is received.

10. The method according to claim 4, wherein performing three-dimensional reconstruction on all the real-time coordinates of the tip to obtain the three-dimensional digital model of the surface profile of the bone model comprises:
  receiving a reconstruction instruction; and
  performing three-dimensional reconstruction on all the real-time coordinates of the tip to obtain the three-dimensional digital model of the surface profile of the bone model based on the reconstruction instruction.

11. A non-transitory computer-readable storage medium storing a computer program, wherein, when the computer program is executed by a processor, acts of the method for generating a surface profile of a bone model according to claim 4 are implemented.

12. An electronic device, at least comprising a memory and a processor, wherein a computer program is stored in the memory, and when the processor executes the computer program in the memory, the method for generating a surface profile of a bone model according to claim 4 is implemented.

13. The method according to claim 6, wherein acquiring the real-time coordinate of the tip of the probe moving on the surface of the bone model based on the real-time center coordinates of the positioning apparatuses acquired by the positioning tracking apparatus comprises:
  determining the real-time coordinate of the tip based on the real-time center coordinates and the fitting relationship.

14. The method according to claim 9, wherein performing three-dimensional reconstruction on all the real-time coordinates of the tip to obtain the three-dimensional digital model of the surface profile of the bone model comprises:
  receiving a reconstruction instruction; and
  performing three-dimensional reconstruction on all the real-time coordinates of the tip to obtain the three-dimensional digital model of the surface profile of the bone model based on the reconstruction instruction.

15. A method for generating a surface profile of a bone model, applied to the apparatus for generating a surface profile of a bone model according to claim 2, comprising:
  acquiring a real-time coordinate of a tip of the probe moving on a surface of a bone model based on real-time center coordinates of the positioning apparatuses acquired by the positioning tracking apparatus; and
  performing three-dimensional reconstruction on all real-time coordinates of the tip to obtain a three-dimensional digital model of a surface profile of the bone model.

16. The method according to claim 15, wherein before acquiring the real-time coordinate of the tip of the probe moving on the surface of the bone model based on the real-time center coordinates of the positioning apparatuses acquired by the positioning tracking apparatus, the method further comprises:
  according to a center coordinate of each positioning apparatus and a geometric dimension of the probe, determining a fitting relationship between the center coordinate of the positioning apparatus and a coordinate of the tip.

17. The method according to claim 16, wherein after determining the fitting relationship between the center coordinate of the positioning apparatus and the coordinate of the tip, the method further comprises:
  calibrating the fitting relationship.

18. A method for generating a surface profile of a bone model, applied to the apparatus for generating a surface profile of a bone model according to claim 3, comprising:
  acquiring a real-time coordinate of a tip of the probe moving on a surface of a bone model based on real-time center coordinates of the positioning apparatuses acquired by the positioning tracking apparatus; and
  performing three-dimensional reconstruction on all real-time coordinates of the tip to obtain a three-dimensional digital model of a surface profile of the bone model.

19. The method according to claim 18, wherein before acquiring the real-time coordinate of the tip of the probe moving on the surface of the bone model based on the real-time center coordinates of the positioning apparatuses acquired by the positioning tracking apparatus, the method further comprises:

according to a center coordinate of each positioning apparatus and a geometric dimension of the probe, determining a fitting relationship between the center coordinate of the positioning apparatus and a coordinate of the tip.

20. The method according to claim 19, wherein after determining the fitting relationship between the center coordinate of the positioning apparatus and the coordinate of the tip, the method further comprises:
calibrating the fitting relationship.

* * * * *